United States Patent
Themelis

(10) Patent No.: US 11,663,716 B2
(45) Date of Patent: May 30, 2023

(54) OPTICAL IMAGING SYSTEM AND CORRESPONDING APPARATUS, METHOD AND COMPUTER PROGRAM

(71) Applicant: Leica Instruments (Singapore) Pte. Ltd., Singapore (SG)

(72) Inventor: George Themelis, Lindau (DE)

(73) Assignee: LEICA INSTRUMENTS (SINGAPORE) PTE., LTD., Singapore (SG)

( * ) Notice: Subject to any disclaimer, the term of this patent is extended or adjusted under 35 U.S.C. 154(b) by 238 days.

(21) Appl. No.: 17/064,945

(22) Filed: Oct. 7, 2020

(65) Prior Publication Data
US 2021/0110538 A1  Apr. 15, 2021

(30) Foreign Application Priority Data

Oct. 10, 2019 (EP) .................................... 19202508

(51) Int. Cl.
*G06T 7/00* (2017.01)
*H04N 23/80* (2023.01)
*H04N 23/63* (2023.01)

(52) U.S. Cl.
CPC ......... *G06T 7/0012* (2013.01); *H04N 23/632* (2023.01); *H04N 23/80* (2023.01); *G06T 2207/30024* (2013.01)

(58) Field of Classification Search
CPC ........ G06T 7/0012; G06T 2207/30024; H04N 23/80; H04N 23/632
See application file for complete search history.

(56) References Cited

U.S. PATENT DOCUMENTS

2012/0184846 A1    7/2012 Izatt et al.
2016/0104030 A1*   4/2016 Matsunami ........ G06V 40/1365
                                                382/115

FOREIGN PATENT DOCUMENTS

DE    102017109202 A1  * 11/2017
DE    102017109202 A1    11/2017
JP         4445598 B2  *  4/2010
KR    20130137064 A   * 12/2013
WO      2018/076094 A1    5/2018

* cited by examiner

*Primary Examiner* — Khai M Nguyen
(74) *Attorney, Agent, or Firm* — 2SPL Patentanwälte PartG mbB; Kieran O'Leary

(57) ABSTRACT

Examples relate to an optical imaging system, and to a corresponding apparatus, method and computer program for an optical imaging system. The optical imaging system comprises one or more information sources for providing information about a current orientation of the optical imaging system towards at least a part of an object of interest. The optical imaging system comprises one or more output modules for providing guidance information for a user of the optical imaging system. The optical imaging system comprises a processing module configured to determine information on a desired orientation of the optical imaging system towards at least a part of the object of interest. The processing module is configured to control the one or more output modules to provide the guidance information for the user of the optical imaging system based on a mismatch between the desired orientation of the optical imaging system towards at least the part of the object of interest and the current orientation of the optical imaging system towards at least the part of the object of interest.

16 Claims, 4 Drawing Sheets

OPTICAL IMAGING SYSTEM AND CORRESPONDING APPARATUS, METHOD AND COMPUTER PROGRAM

CROSS REFERENCE TO RELATED APPLICATIONS

This application claims priority of European patent application number 19202508.8 filed Oct. 10, 2019, the entire disclosure of which is incorporated by reference herein.

TECHNICAL FIELD

Examples relate to an optical imaging system, and to a corresponding apparatus, method and computer program for an optical imaging system.

BACKGROUND

Optical imaging systems, such as surgical microscope, often offer a vast amount of different functions and parameters that can be used to tailor the use of the optical imaging system to the requirements of its users. For example, at a surgical microscope, such parameters may include a direction of observation, a focus or focus point, a zoom level, an illumination intensity and/or an ergonomic position. However, in order to yield an improved operation of the optical imaging system, these functions and parameters may be adjusted and used by the users.

In some surgical microscopes, a robotic arm may be used to provide automatic alignment of the microscope to a predetermined position, which is decided by the user based on a pre-operative three-dimensional scan of the patient. In other words: the surgeon decides, by manually looking at MRI (Magnetic Resonance Imaging) scans, the position and angle of the surgical cavity. This information may be used to guide the robotic arm to align to the predetermined position, thus providing a geometric alignment of the observation position and angle. In many cases, such a functionality is only available in surgical microscopes comprising a robotic arm and an external image-guided system, which might not properly be properly integrated with the microscope.

SUMMARY

There may be a desire for an improved concept for an optical imaging system, in which an operation of the optical imaging system is improved for a user without requiring a robotic arm or image guided system to provide an automatic alignment of the system.

This desire is addressed by the subject matter of the independent claims.

An embodiment of the present disclosure relates to an optical imaging system. The optical imaging system comprises one or more information sources for providing information about a current orientation of the optical imaging system towards at least a part of an object of interest. The optical imaging system comprises one or more output modules for providing guidance information for a user of the optical imaging system. The optical imaging system comprises a processing module configured to determine information on a desired orientation of the optical imaging system towards at least a part of the object of interest. The processing module is configured to control the one or more output modules to provide the guidance information for the user of the optical imaging system based on a mismatch between the desired orientation of the optical imaging system towards at least the part of the object of interest and the current orientation of the optical imaging system towards at least the part of the object of interest.

By providing guidance information for the user optical imaging system, the user is enabled to improve the operation of the optical imaging system, e.g. by properly aligning the optical imaging system with the object of interest. By providing the guidance information based on the mismatch between the desired orientation and the current orientation, the optical imaging system may guide the user to the desired orientation of the optical imaging system.

An embodiment of the present disclosure relates to an apparatus for an optical imaging system. The apparatus may be a part of the optical imaging system that is used to evaluate the information about the current orientation and to provide suitable guidance information. The apparatus comprises an interface for communicating with one or more information sources of the optical imaging system. The one or more information sources are suitable for providing information about a current orientation of the optical imaging system towards at least a part of an object of interest. The interface is further suitable for communicating with one or more output modules of the optical imaging system. The one or more output modules are suitable for providing guidance information for a user of the optical imaging system. The apparatus comprises a processing module configured to determine information on a desired orientation of the optical imaging system towards at least a part of the object of interest. The processing module is configured to control the one or more output modules to provide the guidance information for the user of the optical imaging system based on a mismatch between the desired orientation of the optical imaging system towards at least the part of the object of interest and the current orientation of the optical imaging system towards at least the part of the object of interest.

An embodiment of the present disclosure relates to a corresponding method for an optical imaging system. The method comprises obtaining information about a current orientation of the optical imaging system towards at least a part of an object of interest from one or more information sources of the optical imaging system. The method comprises determining information on a desired orientation of the optical imaging system towards at least a part of the object of interest. The method comprises controlling one or more output modules of the optical imaging system to provide guidance information for a user of the optical imaging system based on a mismatch between the desired orientation of the optical imaging system towards at least the part of the object of interest and the current orientation of the optical imaging system towards at least the part of the object of interest. An embodiment of the present disclosure relates to a corresponding computer program with a program code for performing the method when the computer program is executed on a processor.

BRIEF DESCRIPTION OF THE DRAWING VIEWS

Some examples of apparatuses and/or methods will be described in the following by way of example only, and with reference to the accompanying figures, in which FIG. 1 shows a block diagram of an embodiment of an optical imaging system and of an apparatus for an optical imaging system;

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figure 1:
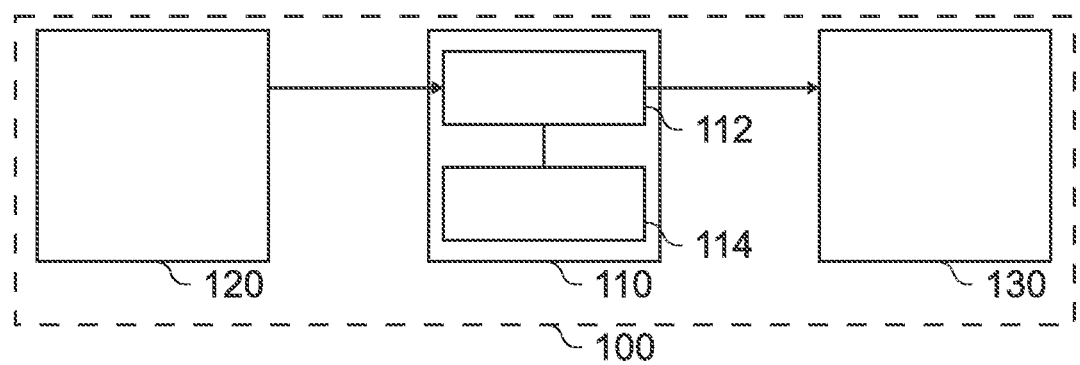

FIG. 1 shows a block diagram of an embodiment of an optical imaging system 100. The optical imaging system 100 comprises one or more information sources 120 for providing information about a current orientation of the optical imaging system 100 towards at least a part of an object of interest. The optical imaging system comprises one or more output modules 130 for providing guidance information for a user of the optical imaging system 100. The optical imaging system further comprises a processing module 114 that is coupled to the one or more information sources 120 and to the one or more output modules 130, e.g. via an interface 112. FIG. 1 further shows an embodiment of an apparatus 110 comprising the processing module 114 and the interface 112, which is coupled to the processing module 114. The interface 112 is suitable for communicating with the one or more information sources 120 of the optical imaging system 100. The interface 112 is further suitable for communicating with the one or more output modules 130. The processing module 114 is configured to determine information on a desired orientation of the optical imaging system 100 towards at least a part of the object of interest. The processing module 114 is configured to control the one or more output modules to provide the guidance information for the user of the optical imaging system 100 based on a mismatch between the desired orientation of the optical imaging system 100 towards at least the part of the object of interest and the current orientation of the optical imaging system 100 towards at least the part of the object of interest.

Embodiments relate to an optical imaging system, and to an apparatus, method and computer program for an optical imaging system. For example, the optical imaging system may be a microscope, e.g. a surgical microscope (system), or the optical imaging system may be an endoscope. In general, a microscope is an optical instrument that is suitable for examining objects that are too small to be examined by the human eye (alone). For example, a microscope may provide an optical magnification of an object, such as the sample of organic tissue. In modern microscopes, the optical magnification is often provided for a camera or an imaging sensor. In other words, the optical imaging system 100 may further comprise one or more optical magnification components that are used to magnify a view on the sample of organic tissue. For example, the optical imaging system 100 may be a microscope for use in a laboratory, e.g. a microscope that may be used to examine the sample of organic tissue in a petri dish. Alternatively, the optical imaging system 100 may be a surgical microscope, e.g. a system comprising a microscope that is to be used during a surgical procedure. Although embodiments are mainly described in connection with a surgical microscope, they may also be applied, in a more general manner, to any optical imaging system comprising one or more information sources and one or more output modules.

The processing module 114 is configured to determine the information on a desired orientation of the optical imaging system 100 towards at least a part of the object of interest. In general, the orientation of the optical imaging system may comprise one or both of the following components: a three-dimensional angular orientation of the optical imaging system towards at least the part of the object of interest, which may, for example, be defined relative to a three-dimensional coordinate system, e.g. as a vector in a three-dimensional coordinate system, and a distance between the optical imaging system and at least the part of the object, e.g. an Euclidian distance and/or a distance along the vector defined by the three-dimensional orientation of the optical imaging system. The desired orientation of the optical imaging system 100 towards at least the part of the object of interest may be an orientation, in which an operation of the optical imaging system is improved, i.e. in which an utility of the optical imaging system is improved, as the parameters and/or orientation of the optical imaging system is/are suitable for the task at hand. For example, the optical imaging system may be a surgical microscope, i.e. a system comprising a microscope that is suitable for use during surgery. In this case, the object of interest may be a body, e.g. a body of a (human) patient. By providing a guidance for an orientation of the optical imaging system towards the part of the body, an operation of the optical imaging system for a user, e.g. a surgeon, may be improved. For example, during surgery, the surgical microscope may be used, by a surgeon, to examine a wound tract that surgery is performed on, or in more general terms, the surgical site or an incision at the surgical site. In this case, the desired of the optical imaging system 100 may be an orientation, in which the surgeon is able to examine the wound tract or surgical site. For example, the desired orientation of the optical imaging system 100 may be chosen such, that the wound tract or surgical site is located within a field of view of the optical imaging system. Additionally, the desired orientation of the optical imaging system 100 may be chosen such, that the wound tract or surgical site is examinable without touching the body, e.g. as the orientation is chosen such that the field of view follows the wound tract. In general, the orientation of the optical imaging system 100 towards the wound, incision and/or surgical site of the body may comprise at least one of a distance between the optical imaging system 100 and the wound, incision and/or surgical site of the body and a three-dimensional angular orientation of the optical imaging system 100 towards the wound, incision and/or surgical site of the body. This may provide an improved field of view for the surgeon, e.g. based on the size, location and orientation of the wound, incision or surgical site.

In at least some embodiments, the desired orientation of the optical imaging system is based on a functionality being used. For example, a different orientation may be desired in cases where fluorescence imaging is performed than in cases, in which merely an overview of the object of interest is sought. Accordingly, the processing module 114 may be configured to determine the desired orientation of the optical imaging system based on a currently active functionality of the optical imaging system 100.

When surgery is performed, in many cases, a pre-operative (i.e. before the surgical procedure) scan is taken that is used to plan the surgical procedure. In many cases, this pre-operative scan is a Magneto-Resistance Imaging (MRI) scan, but sometimes, an angiography scan, an ultrasound scan or preoperative planning data may be used (e.g. in addition or as an alternative). Within the scan, the diseased tissue or broken bone may be visible, enabling the surgeon to plan an incision they are taking to gain access to the diseased tissue or broken bone. Based on this plan, the desired orientation of the optical imaging system may also be determined. In other words, the processing module 114 may be configured to determine the desired orientation of the optical imaging system 100 towards at least the part of the body based on a pre-operative scan of at least the part of the body. The pre-operative scan may be used to determine the desired orientation of the optical imaging system, e.g. so that a wound or site of a surgery can be inspected by the surgeon. Using the pre-operative scan of at least the part of the body, an optimal or preferred position and/or angle of the surgical cavity may be determined (i.e. the desired orientation) in order to reach the lesion (i.e. wound) with the least damage to healthy tissue. For example, the desired orientation of the optical imaging system may be chosen by the surgeon based on the pre-operative scan, and input into the optical imaging system. In other words, the processing module may be configured to determine the desired orientation based on an input of a user of the optical imaging system, the input being based on the pre-operative scan of at least the part of the body. Alternatively, the desired orientation of the optical imaging system may be automatically determined by the optical imaging system. In other words, the processing module 114 may be configured to automatically or autonomously (i.e. without intervention by a user of the optical imaging system) determine the desired operation of the optical imaging system 100 towards at least the part of the body based on a location of at least one of diseased tissue, a tumor or a broken bone within the pre-operative scan of at least the part of the body. Accordingly, the processing module may be configured to detect at least one of diseased tissue, a tumor or a broken bone within the pre-operative scan of at least the part of the body, and to base the determination of the desired orientation of the optical imaging system on the detected deceased tissue, tumor, or broken bone.

In many cases, it may be useful (or required) to change the desired orientation during surgery, e.g. as the surgical procedure proceeds. Additionally, in some cases, the wound tract may be difficult to navigate with the optical imaging system. In such cases, an intra-operative (i.e. during the surgical procedure) three-dimensional scan may be used to determine the desired orientation of at least the part of the body. For example, the one or more information sources 120 may comprise a tissue scanner configured to provide an intra-operative three-dimensional scan of the at least the part of the body. The processing module 114 may be configured to determine the desired orientation of the optical imaging system 100 towards at least the part of the body based on the intra-operative three-dimensional scan of the at least the part of the body. For example, the processing module 114 may be configured to determine an improved (e.g. an optimal) viewing angle and/or field of view towards the wound, wound tract, incision or surgical site based on the intra-operative three-dimensional scan of the at least part of the body, and to determine the desired orientation of the optical imaging system based on the improved viewing angle and/or field of view towards the wound, wound tract, incision or surgical site. The intra-operative three-dimensional scan may be used to adjust the optical imaging system during surgery, e.g. to adjust the optical imaging system as the surgery proceeds, and/or to provide an improved orientation towards close spaces, such as wound tracts.

Embodiments of the present disclosure are based on detecting a mismatch between the desired orientation of the optical imaging system and the current orientation of the optical imaging system. The current orientation of the optical imaging system is determined using the one or more information sources 120 of the optical imaging system. The one or more information sources 120 for providing information about a current orientation of the optical imaging system 100 towards at least a part of an object of interest. If the object of interest is at least a part of a body, the one or more information sources 120 may be suitable for providing information about a current orientation of the optical imaging system 100 towards at least the part of the body. For example, as shown above, the optical imaging system may be a surgical microscope, which may be used to examine a wound, incision or surgical site of the body. Accordingly, the one or more information sources 120 may be suitable for providing information about a current orientation of the optical imaging system 100 towards the wound, incision and/or surgical site of the body. The wound, incision or surgical site may be the object of interest to be examined by a user of the optical imaging system.

In various embodiments, a camera image of at least the part of the body may be used to determine the current orientation of the optical imaging system towards at least the part of the body. For example, the camera image may be used to determine a quality of the current orientation of the optical imaging system towards at least the part of the body, e.g. with regards to a focus, a zoom level, a field of view etc.

Accordingly, the one or more information sources 120 may comprise a camera configured to provide a camera image of at least the part of the body. In many cases, the camera may be a camera suitable for providing two-dimensional camera images, e.g. a main camera or an auxiliary camera of a surgical microscope. In some embodiments, two or more cameras may be used to provide two or more camera images, which are subsequently used to determine the current orientation of the optical imaging system. In general, the camera may comprise an APS (Active Pixel Sensor)- or a CCD (Charge-Coupled-Device)-based imaging sensor module. For example, in APS-based imaging sensor modules, light is recorded at each pixel using a photodetector and an active amplifier of the pixel. APS-based imaging sensor modules are often based on CMOS (Complementary Metal-Oxide-Semiconductor) or S-CMOS (Scientific CMOS) technology. In CCD-based imaging sensor modules, incoming photons are converted into electron charges at a semiconductor-oxide interface, which are subsequently moved between capacitive bins in the imaging sensor modules by a control circuitry of the sensor imaging module to perform the imaging. Alternatively, or additionally, the camera may be a depth-sensing camera or comprise a depth sensor, suitable for providing a depth-sensing camera image. Accordingly, the camera image may be a depth-sensing camera image or comprise a two-dimensional and a depth-sensing component. For example, the camera may comprise a depth sensor, e.g. a Time of Flight-based depth sensor or a structured light-based depth sensor. The information about the current orientation of the optical imaging system 100 may comprise the camera image. The camera image may be used to examine the orientation of the optical imaging system towards the object of interest, e.g. in order to determine one or more ways of improving the orientation.

After acquiring the camera image, the camera image may be processed to determine the quality of the current orientation (and/or of current operating settings) of the optical imaging system. In this context, the "quality of the current orientation" may be an index that indicates how suitable the current orientation (or the current operating settings) is/are for the task at hand. For example, the camera image may be a camera image of a wound, wound tract, incision or surgical site. Based on the camera image, which may correspond to the field of view available to the surgeon at the current orientation, the optical imaging system may determine whether the focus is at the right point (e.g. the wound, wound tract, incision or surgical site), whether the field of view covers the object of interest (e.g. the wound, wound tract, incision or surgical site), whether the field of view is chosen too small (so not the entire object of interest is examinable) or too large (so smaller details are not visible to the surgeon), or whether the imaging axis is suitable for the task at hand (e.g. in situations, in which the inside of a wound tract is examined). Accordingly, the processing module 114 may be configured to process the camera image to determine at least one of a quality of a focus (i.e. whether the focus is at the right point), a utility of a current zoom level (i.e. whether the field of view covers the object of interest, whether the field of view is chosen too small or too large), and an alignment of an imaging axis of the camera with at least the part of the object (i.e. whether the imaging axis is suitable for the task at hand). The processing module 114 may be configured to control the one or more output modules to provide the guidance information based on the quality of the current orientation (or operating settings) of the optical imaging system, i.e. based on at least one of the quality of the focus, the utility of the current zoom level, and the alignment of an imaging axis of the camera with at least the part of the object. This may help the user to better position and/or operate the optical imaging system.

In at least some embodiments, the one or more information sources 120 may also be suitable for providing information about one or more current operating settings of the optical imaging system 100. For example, the one or more information sources 120 may comprise a central control unit of the optical imaging system, e.g. of the surgical microscope, configured to provide the information about the one or more current operating settings of the optical imaging system. The information about the one or more current operating settings may comprise one or more elements of the group of information about a current angular orientation of the optical imaging system, information about a current focus of the optical imaging system, information about a current zoom (level) of the optical imaging system, information about a current illumination level of the optical imaging system, and information about a current spot size of an illumination of the optical imaging system. The processing module 114 may be configured to determine the current orientation of the optical imaging system based on the information about the one or more current operating settings. Furthermore, the processing module 114 may be configured to determine the current orientation of the optical imaging system based on the pre-operative scan of the at least part of the body. For example, the processing module 14 may be configured to align the camera image with the pre-operative scan of at least part of the body to determine the current orientation of the optical imaging system towards at least the part of the body.

The processing module 114 is configured to control the one or more output modules to provide the guidance information for the user of the optical imaging system 100 based on the mismatch between the desired orientation of the optical imaging system 100 towards at least the part of the object of interest and the current orientation of the optical imaging system 100 towards at least the part of the object of interest. Accordingly, the processing module 114 may be configured to determine the mismatch between the desired orientation of the optical imaging system 100 and the current orientation of the optical imaging system. As introduced above, the orientation of the optical imaging system may comprise one or both of the two components three-dimensional angular orientation of the optical imaging system and distance between the optical imaging system and the at least part of the object of interest. Accordingly, the processing module may be configured to determine a difference between the desired three-dimensional angular orientation of the optical imaging system towards at least the part of the object of interest and the current desired three-dimensional angular orientation of the optical imaging system towards at least the part of the object of interest. The processing module may be configured to determine a difference between the desired distance between the optical imaging system and the at least part of the object of interest and the current distance between the optical imaging system and the at least part of the object of interest. The mismatch between the desired orientation of the optical imaging system and the current orientation of the optical imaging system may be based on one or both of the difference between the desired three-dimensional angular orientation of the optical imaging system towards at least the part of the object of interest and the current desired three-dimensional angular orientation of the optical imaging system towards at least the part of the object of interest and the difference between the desired distance between the optical imaging system and the at least part of the object of interest and the current distance between the optical imaging system and the at least part of the object of interest.

Based on the mismatch, the output modules are controlled to provide guidance information for the user of the optical imaging system. In general, the guidance information may be information suitable for instructing the user of the optical imaging system about how to adjust the optical imaging system in order to reach the desired orientation of the optical imaging system, or suitable for instructing the user of the optical imaging system about how to adjust the optical imaging system in order to reduce the difference between desired orientation of the optical imaging system and the current orientation of the optical imaging system. For example, the guidance information may comprise one or more tactile, visual or auditory instructions or affordances suitable for guiding the user of the optical imaging system. The processing module 114 may be configured to generate the guidance information based on the mismatch between the desired orientation of the optical imaging system and the current orientation of the optical imaging system.

The guidance information is provided via the one or more output modules 130. For example, the one or more output modules 130 may comprise at least one of one or more displays (for providing the one or more visual instructions or affordances), one or more indicator lights (for providing the one or more visual instructions or affordances), one or more vibration modules (for providing the one or more tactile instructions or affordances), and one or mode audio output modules (for providing the one or more auditory instructions or affordances). For example, the processing module may be configured to control the one or more displays to display one or more arrows for guiding the adjustment of the optical imaging system. The one or more arrows may indicate a direction in which the optical imaging system is to be moved and/or tilted to approach or reach the desired orientation of the optical imaging system. Additionally or alternatively, the one or more indicator lights may be arrow-shaped or may indicate a direction the optical imaging system is to be moved and/or tilted to approach or reach the desired orientation of the optical imaging system. The processing module may be configured to control the one or more indicator lights to indicate a direction the optical imaging system is to be moved and/or tilted to approach or reach the desired orientation of the optical imaging system. Additionally or alternatively, the processing module may be configured to control the one or more vibration modules to guide the user towards the desired orientation of the optical imaging system. For example, the processing module may be configured to control the one or more vibration modules such, that a vibration of the one or more vibration modules increases if the optical imaging system is moved away from the desired orientation of the optical imaging system, and so that the vibration decreases if the optical imaging system is moved towards the desired orientation of the optical imaging system. The one or more audio output modules, e.g. loudspeakers, may be used similarly. For example, the processing module may be configured to control the one or more audio output modules such, that a repetition rate or frequency of sound output by the one or more audio output modules increases if the optical imaging system is moved towards the desired orientation of the optical imaging system, and so that the that a repetition rate or frequency of sound decreases if the optical imaging system is moved away from the desired orientation of the optical imaging system (or vice versa), e.g. similar to a park assistance feature of a vehicle. Alternatively or additionally, the sound of two or more audio output modules may be used to guide the user, e.g. the processing module may be configured to control the two or more audio output modules such, that sound is emitted from a direction, in which the optical imaging system is to be moved to approach or reach the desired orientation of the optical imaging system.

In at least some embodiments, the guidance information may be used to call the attention of the user to certain areas of at least the part of the object of interest. For example, during surgery, a bleeding may be detected in the camera image, and the surgeon may be alerted to the bleeding using the guidance information. Additionally, the desired orientation may change based on the detected bleeding. In other words, the processing module 114 may be configured to detect one or more events or objects within the camera image. For example, the one or more events or objects may comprise bleeding that is visible within the camera image, and/or one or more foreign objects, foreign substances and/or foreign bodies within the wound, wound tract or surgical site. The processing module 114 may be configured to control the one or more output modules to provide the guidance information based on the one or more detected events or objects. For example, the guidance information provided in response to the detected one or more events or objects may indicate a location and/or a type of the one or more detected events or objects relative to at least the part of the object of interest. Additionally, by detecting the one or more events or objects, the orientation of the optical imaging system may be adjusted during operation of the optical imaging system to accommodate for the events or objects. Accordingly, the processing module 114 may be configured to update and/or change the desired orientation of the optical imaging system based on the one or more detected events or objects, and to control the one or more output modules to provide the guidance information based on the updated/changed desired orientation of the optical imaging system.

In at least some embodiments, not only the physical orientation of the optical imaging system may be adjusted to improve the operation of the optical imaging system, but also the operating settings may be adjusted accordingly. In this context, the term "operating settings" is used, which may be used for a single operating setting as well as multiple operating settings. Accordingly, the operating settings may be one or more operating settings. For example, the desired orientation of the optical imaging system may be associated with corresponding operating settings, which are suitable for operating the optical imaging system in the desired orientation of the optical imaging system, e.g. that are improved or optimal operating settings at the desired orientation of the optical imaging system. For example, the operating settings may comprise one or more of a focus of the optical imaging system, a zoom (level) of the optical imaging system, an illumination level of the optical imaging system, and a spot size of an illumination of the optical imaging system. For example, in case the optical imaging system is a surgical microscope, the operating settings of the optical imaging system 100 may comprise at least one of a zoom level of the microscope, a working distance of the microscope, and an illumination level of the microscope.

The processing module 114 may be configured to provide, via the one or more output modules, suitable guidance information for adjusting the operating settings of the optical imaging system. Again, the guidance information may be based on a mismatch between current operating settings and the operating settings associated with the desired orientation of the optical imaging system. For example, the one or more information sources 120 may be suitable for providing information about one or more current operating settings of the optical imaging system 100. In case the optical imaging system is a surgical microscope, the information about the one or more current operating settings of the optical imaging system 100 may comprise at least one of information about a zoom level of the microscope, information about a working distance of the microscope, and information about an illumination level of the microscope. The processing module 114 may be configured to determine operating settings of the optical imaging system 100 associated with the desired orientation of the optical imaging system 100 towards at least the part of the object of interest. For example, the processing module 114 may be configured to determine at least one of a zoom level of the microscope associated with the desired orientation of the optical imaging system, a working distance of the microscope associated with the desired orientation of the optical imaging system, and an illumination level of the microscope associated with the desired orientation of the optical imaging system. For example, the processing module 114 may be configured to determine the operating settings of the optical imaging system 100 associated with the desired orientation of the optical imaging system 100 by retrieving the operating settings from a database based on the desired orientation of the optical imaging system, or by using the desired orientation of the optical imaging system as parameters for one or more formulae to calculate the operating parameters associated with the desired orientation of the optical imaging system. For example, fluorescence imaging, a functionality of surgical microscopes, is not optimally performed at the furthest working distances, but at smaller working distances. Such information may be stored in the database, and retrieved based on the desired orientation of the optical imaging system.

The processing module 114 may be configured to control the one or more output modules to provide the guidance information for the user of the optical imaging system 100 based on a mismatch between the one or more current operating settings of the optical imaging system 100 and the one or more operating settings of the optical imaging system 100 associated with the desired orientation of the optical imaging system 100. Accordingly, the processing module 114 may be configured to determine the mismatch between the one or more current operating settings of the optical imaging system 100 and the one or more operating settings of the optical imaging system 100 associated with the desired orientation of the optical imaging system 100, e.g. by comparing the current operating settings with the operating settings associated with the desired orientation of the optical imaging system. The guidance information may comprise one or more tactile, visual or auditory instructions or affordances suitable for guiding the user of the optical imaging system to change the operating settings to the operating settings associated with the desired orientation of the optical imaging system, e.g. by prompting the user whether to change the operating settings to the operating settings associated with the desired orientation of the optical imaging system. By incorporating the operating settings of the optical imaging system, embodiments may be used to not only improve the orientation of the optical imaging system towards the object of interest, but also parameters used to operate the optical imaging system.

In some cases, the orientation of the optical imaging system chosen by its user may be suitable for the task, but may lead to instabilities within the optical imaging system, e.g. within the surgical microscope system, as the arm of the surgical microscope is close to losing balance. Thus, the optical imaging system may be prone to vibrating, which may inhibit the operation of the optical imaging system. For example, such vibrations may be detected using accelerometers, which are configured to detect accelerative forces, such as vibrations, affecting the optical imaging system. Accordingly, the one or more information sources 120 may comprise an accelerometer of the optical imaging system 100. The accelerometer may be configured to provide information about a vibrational movement of the optical imaging system 100. The processing module 114 may be configured to control the one or more output modules to provide the guidance information based on the information about the vibrational movement of the optical imaging system 100. For example, the processing module 114 may be configured to change or update the desired orientation of the optical imaging system based on the information about the vibration movement of the optical imaging system, e.g. such that the desired orientation of the optical imaging system is less vibration-prone than the current orientation of the optical imaging system. Based on the vibrational movement of the optical imaging system, the user may be provided with an alternative orientation (or geometry) of the optical imaging system, in which the vibrations, e.g. of an arm of the optical imaging system, are reduced.

In at least some embodiments, the guidance information may be provided based on one or more user preferences of a user of the optical imaging system. For example, some users may prefer auditory indications, while some users prefer visual indicators. In other words, the processing module 114 may be configured to generate the guidance information based on one or more user preferences of the user of the optical imaging system. For example, the one or more user preferences may indicate a preference of a user of the optical imaging system as to which output module or output modules is/are to be used for providing the guidance information.

In at least some embodiments, the guidance information may also be generated based on artificial intelligence, e.g. using a machine-learning model. For example, the machine-learning model may be used to derive the one or more user preferences from a previous use of the optical imaging system. Alternatively or additionally, the machine-learning model may be used to calculate the operating settings associated with the desired orientation of the optical imaging system, or to determine the desired orientation of the optical imaging system based on pre-operative scan of at least the part of the body and the functionality of the optical imaging system being used, e.g. by making a prediction about which portion of at least the part of the body the user intends to examine.

The interface 112 may correspond to one or more inputs and/or outputs for receiving and/or transmitting information, which may be in digital (bit) values according to a specified code, within a module, between modules or between modules of different entities. For example, the interface 12 may comprise interface circuitry configured to receive and/or transmit information. In embodiments the processing module 114 may be implemented using one or more processing units, one or more processing devices, any means for processing, such as a processor, a computer or a programmable hardware component being operable with accordingly adapted software. In other words, the described function of the processing module 114 may as well be implemented in software, which is then executed on one or more programmable hardware components. Such hardware components may comprise a general purpose processor, a Digital Signal Processor (DSP), a micro-controller, etc.

More details and aspects of the optical imaging system and the apparatus are mentioned in connection with the proposed concept or one or more examples described above or below (e.g. FIGS. 2 to 4). The optical imaging system and the apparatus may comprise one or more additional optional features corresponding to one or more aspects of the proposed concept or one or more examples described above or below.

Figure 2:
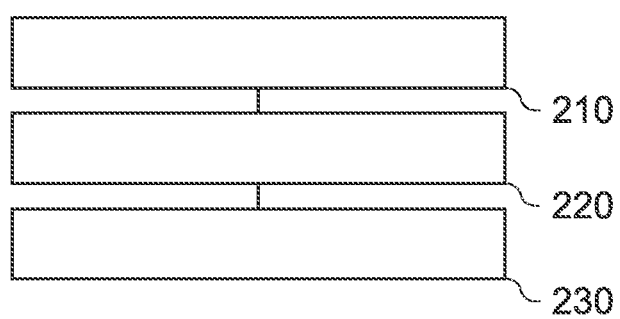
FIG. 2 shows a flow chart of an embodiment of a method for an optical imaging system.

FIG. 2 shows a flow chart of an embodiment of a corresponding method, e.g. a computer-implemented method, for an optical imaging system, e.g. the optical imaging system 100 of FIG. 1. Although the aspects of the optical imaging system 100 have been described in the context of an apparatus, it is clear that these aspects also represent a description of the corresponding method, where a property or functional feature of the apparatus corresponds to a method step or a feature of a method step. The method comprises obtaining 210 information about a current orientation of the optical imaging system 100 towards at least a part of an object of interest from one or more information sources 120 of the optical imaging system 100. The method comprises determining 220 information on a desired orientation of the optical imaging system 100 towards at least a part of the object of interest. The method comprises controlling 230 one or more output modules of the optical imaging system 100 to provide guidance information for a user of the optical imaging system 100 based on a mismatch between the desired orientation of the optical imaging system 100 towards at least the part of the object of interest and the current orientation of the optical imaging system 100 towards at least the part of the object of interest. As indicated above, features described in connection with the optical imaging system 100 of FIG. 1 may be likewise applied to the method of FIG. 2.

More details and aspects of the method are mentioned in connection with the proposed concept or one or more examples described above or below (e.g. FIG. 1, 3 or 4). The method may comprise one or more additional optional features corresponding to one or more aspects of the proposed concept or one or more examples described above or below.

Embodiments provide a microscope function, or more general a function for an optical imaging system, for guiding a user to an improved operation of the microscope, such as positioning the optics carrier to an improved position, adjusting a focus and zoom, and drawing attention on specifying events like bleeding.

Embodiments of the present disclosure provide a set of features that may enable a more efficient use of the microscope. More specifically, embodiments may use communication modules (visual, audio, vibration, e.g. the one or more output modules) to guide the surgeon to achieve an improved alignment of the microscope.

Figure 3:
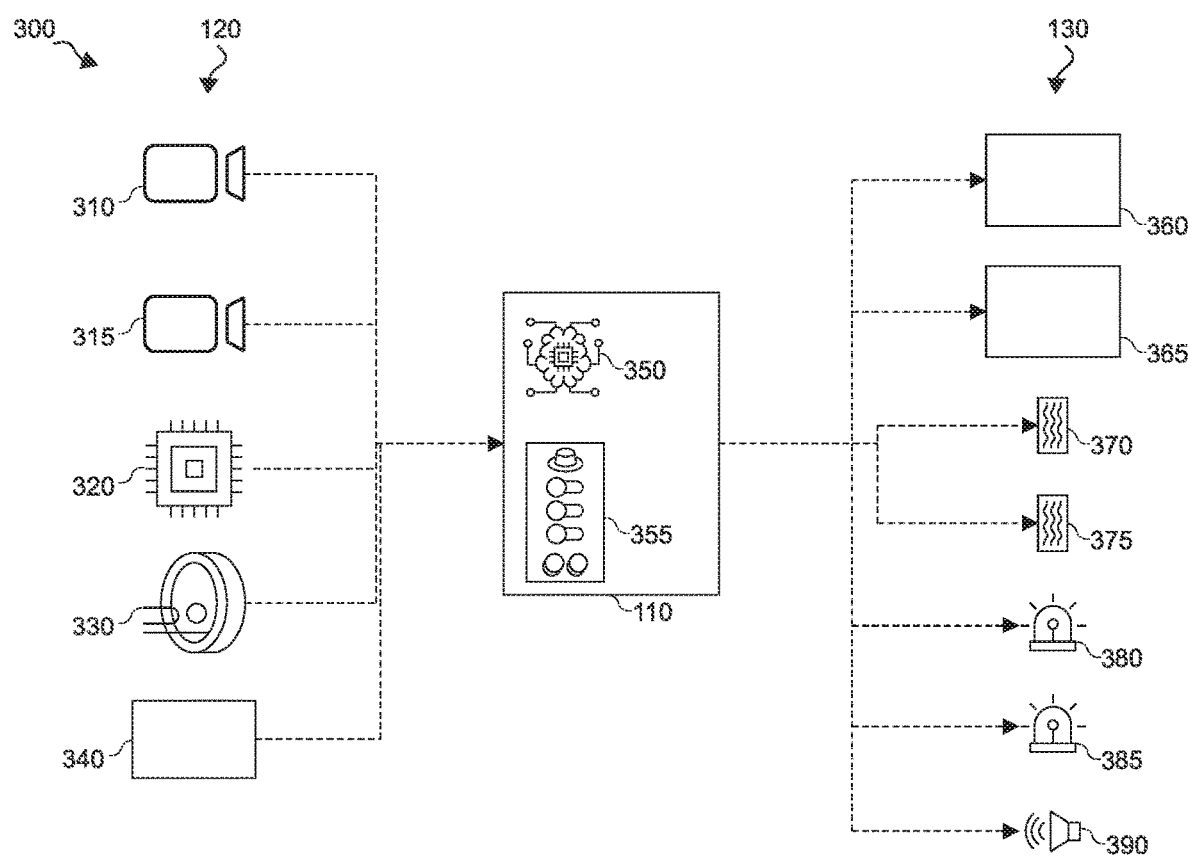
FIG. 3 shows a schematic diagram of an optical imaging system according to an embodiment.

FIG. 3 shows a schematic diagram of a microscope 300, such as a surgical microscope, according to an embodiment. The microscope 300 may be an implementation of the optical imaging system 100 of FIG. 1. The basic implementation may comprise one or more of the following components:

One or more information sources 120 such as one or more cameras 310; 315 (e.g. a main camera 310 of the microscope and one or more other cameras 315), a microscope control unit 320 (which may collect microscope settings such as focus, zoom, illumination), and preoperative data (e.g. MM) 330. In addition, one or more other sensors 340 may be used.

The feed (i.e. camera image/images) of the camera/cameras 310; 315 may be used to determine parameters a focus quality, zoom (e.g. whether the surgical cavity is (optimally) covered by the field of view), whether the imaging axis is properly aligned to the surgical cavity, and/or to detect events/objects for which the surgeon must be informed about, e.g. bleeding.

The microscope control unit 320 may provide information about a zoom, a working distance, and an illumination intensity. This information may be useful for determining whether the user is using the microscope under optimal conditions. For example, a use of fluorescence imaging might not be optimal performed at the furthest working distances.

Additionally or alternatively, preoperative data 330, e.g. an MRI scan, an angiography scan, an ultrasound, or preoperative planning may be used. Using the preoperative data, an improved or preferred position and/or angle of the surgical cavity may be determined in order to reach the lesion with the least damage to healthy tissue (e.g. as desired orientation of the microscope 300).

Other sensors 340 might also include one or more accelerometers to measure the microscope vibrations, and perhaps suggest another geometry which can reduce the vibrations of the microscope's arm. The other sensors might also comprise one or more 3D tissue scanners which might allow to align the field of view to a less obstructed view within a narrow and deep surgical cavity.

The microscope 300 may also comprise a guidance processing unit 110 (e.g. the apparatus 110 of FIG. 1) which may be configured to process (all) data, and which may use user's settings/preferences 350, and Artificial Intelligence 355 to determine what feedback/guidance to provide to the user. Although, conceptually, this is a separate processor unit, physically it might be part of the microscope's main processing unit, i.e. this might be a software module running on a main powerful computer, in parallel with other processing threads.

The microscope 300 may also comprise one or more of the following: a set of feedback/guidance units 130 (e.g. the one or more output modules, such as one or more displays 360; 365 (e.g. a main display 360 of the microscope and one or more auxiliary displays 365), one or more vibration modules 370; 375, one or more warning/indication lights 380, and one or more audio modules 390. These parts might be added to the microscope specifically for this function. Examples of different modules to be used may include:

One or more dedicated display(s) 360; 365 on the microscope, e.g. on the optical carrier or the arm, for easier visual access by the user. The displays/screens could be used to display at least one of an indication of whether the system is in optimal settings/alignment or requires improvement, instructions on how to improve the settings/alignment, e.g. by displaying arrows indicating in which direction the user may move/tilt the optics carrier in order to achieve an improved imaging geometry (i.e. orientation of the microscope), or to achieve the alignment decided in preoperative planning, or to draw user's attention to a specific point where something worth noticing, such as bleeding, or an area of fluorescence which was not previously visible, so the surgeon might have missed. In other words, in at least some embodiments, navigation arrows displayed on the microscope may be used to align the microscope.

One or more vibration modules 370; 375 (e.g. similar to vibrations modules used in mobile phones), which could warn a user when moving the microscope. For example, when a user is moving or tilting the optics carrier, he or she could chose to look at the video display, rather than the arrows. In that case, the microscope may provide a feedback on whether the position is close to, or on the desired (e.g. optimal) position. For example, a vibration may indicate that the user should not move further. Furthermore, separate modules on the right and left handles may provide more intuitive feedback as to the direction the microscope needs to be moved to.

One or more audio modules 390 may also provide feedback in a similar way as the vibration modules. For example, the one or more audio modules 390 may be used similar to a parking assistant of the car, which is used to help a user when parking the car, by using a variable frequency and intensity. Again, multiple speakers may provide stereo/spatial/directional feedback. One or more warning signs such as LEDs (Light Emitting Diodes) 380 may also serve the same purpose.

Figure 4:
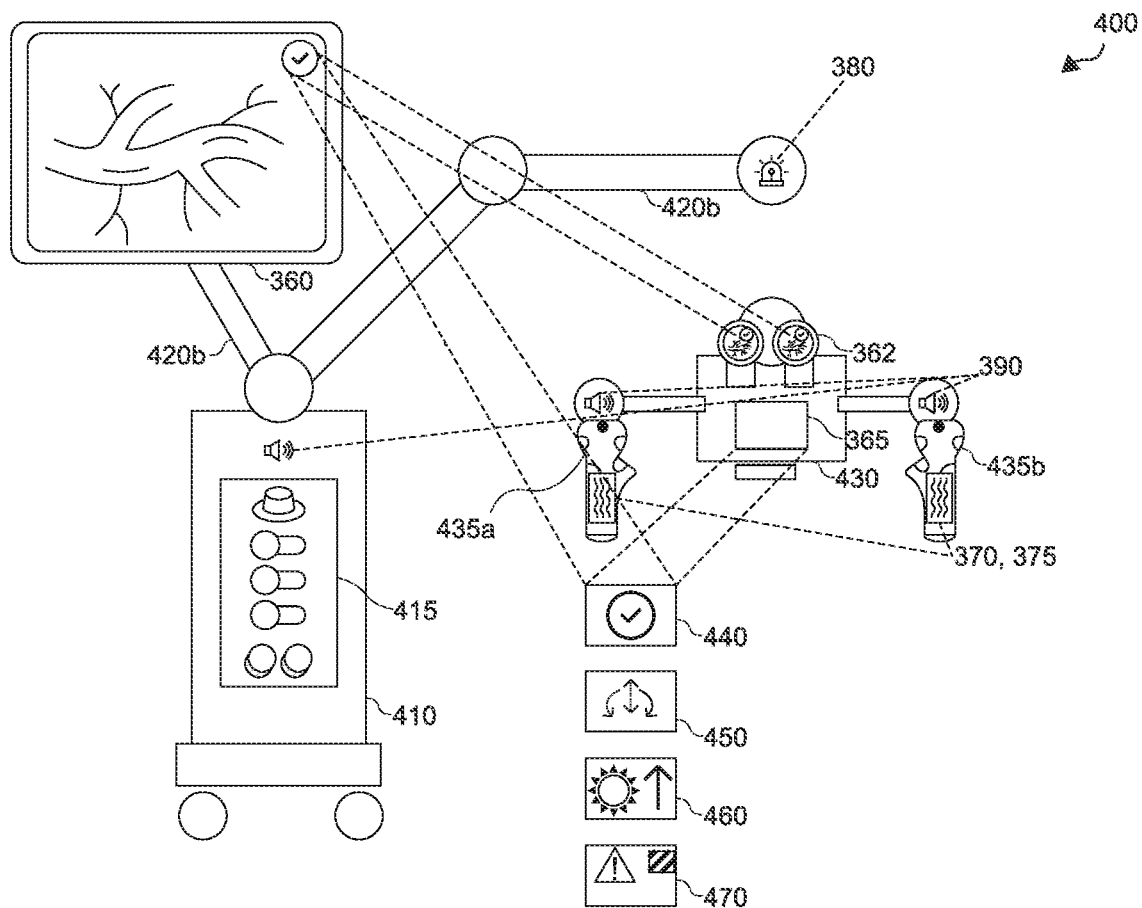
FIG. 4 shows a schematic diagram of a surgical microscope according to an embodiment.

FIG. 4 shows a schematic diagram of a surgical microscope 400 according to an embodiment. In FIG. 4, the components of the microscope 300 are shown at their respective positions at the microscope. The surgical microscope 400 comprises a base unit 410 with controls 415 and a speaker 390. The surgical microscope 400 further comprises two arms 420a; 420b, one (420a) for holding a main display 360 of the surgical microscope and one (420b) for holding the microscope 430 of the surgical microscope, this arm further comprising an LED indication 380. The microscope comprises dual viewfinders 362 showing the same image as the main display 360, and an auxiliary display 365. Affixed to the microscope 430, two adjustment handles 435a; and 435b are included, each comprising a speaker 390 and a vibration module 370; 375. On the auxiliary display 365 and/or on the main display 360, different guidance information may be displayed. For example, as shown at reference sign 440, a sign indicating that the orientation is OK/aligned may be displayed. As shown at reference sign 450, arrows may be displayed that may be followed to move or tilt the OC. As shown at reference sign 460, a visual indicator may be shown to guide the user to increase the illumination intensity. As shown at reference sign 470, an indication may be shown that alerts the user of bleeding in the top-right corner of the field of view.

More details and aspects of the surgical microscope are mentioned in connection with the proposed concept or one or more examples described above or below (e.g. FIGS. 1 to 3, 5). The surgical microscope may comprise one or more additional optional features corresponding to one or more aspects of the proposed concept or one or more examples described above or below.

Figure 5:
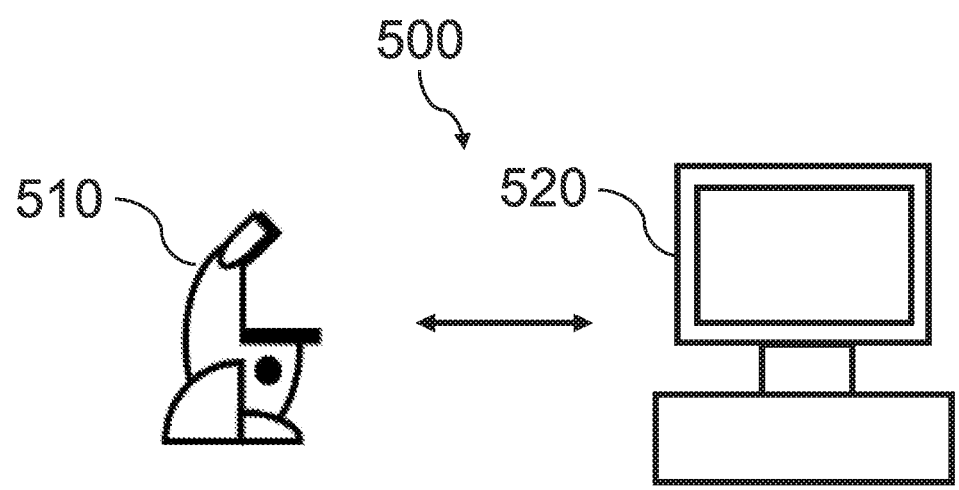
FIG. 5 shows a schematic diagram of a system comprising a microscope and a computer system.

Some embodiments relate to a microscope comprising a system as described in connection with one or more of the FIGS. 1 to 4. Alternatively, a microscope may be part of or connected to a system as described in connection with one or more of the FIGS. 1 to 4. FIG. 5 shows a schematic illustration of a system 500 configured to perform a method described herein. The system 500 comprises a microscope (or optical imaging system) 510 and a computer system 520. The microscope (or optical imaging system) 510 is configured to take images and is connected to the computer system 520. The computer system 520 is configured to execute at least a part of a method described herein. The computer system 520 may be configured to execute a machine learning algorithm. The computer system 520 and microscope 520 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 520 may be part of a central processing system of the microscope (or optical imaging system) 510 and/or the computer system 520 may be part of a subcomponent of the microscope (or optical imaging system) 510, such as a sensor, an actor, a camera or an illumination unit, etc. of the microscope (or optical imaging system) 510.

The computer system 520 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 520 may comprise any circuit or combination of circuits. In one embodiment, the computer system 520 may also include a display device, one or more speakers, and a keyboard and/or controller, which can include a mouse, trackball, touch screen, voice-recognition device, or any other device that permits a system user to input information into and receive information from the computer system 520 may also include a display device, one or more speakers, and a keyboard and/or controller, which can include a mouse, trackball, touch screen, voice-recognition device, or any other device that permits a system user to input information into and receive information from the computer system 520 may also include a display device, one or more speakers, and a keyboard and/or controller, which can include a mouse, trackball, touch screen, voice-recognition device, or any other device that permits a system user to input information into and receive information from the computer system 520 may also include a display device, one or more speakers, and a keyboard and/or controller, which can include a mouse, trackball, touch screen, voice-recognition device, or any other device that permits a system user to input information into and receive information from the computer system 520.

More details and aspects of the system, of the microscope/optical imaging system and/or of the computer system are mentioned in connection with the proposed concept or one or more examples described above or below (e.g. FIGS. 1 to 4). The system, microscope/optical imaging system or computer system may comprise one or more additional optional features corresponding to one or more aspects of the proposed concept or one or more examples described above or below.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS

100 Optical imaging system
110 Apparatus for an optical imaging system
112 Interface
114 Processing module
120 One or more information sources
130 One or more output modules
210 Obtaining information about a current orientation of an optical imaging system
220 Determining information about a desired orientation of the optical imaging system
230 Controlling one or more output modules to provide guidance information
300 (Surgical) microscope
310 Camera
315 Camera
320 Microscope control unit
330 Preoperative data
340 One or more other sensors
350 User settings/preferences
355 Artificial Intelligence
360 Main display of a microscope
362 Viewfinder
365 Auxiliary display of a microscope
370 Vibration module
375 Vibration module
380 One or more warning/indication lights
390 One or more audio modules
400 Surgical microscope
410 Base unit
420a; 420b Arms of the surgical microscope
430 Microscope
435a; 435b Adjustment handles
440-470 Visual indications
500 System
510 Microscope or optical imaging system
520 Computer system

What is claimed is:
1. An optical imaging system comprising:
one or more information sources for providing information about a current orientation of the optical imaging system towards at least a part of an object of interest;
one or more outputs for providing guidance information for a user of the optical imaging system; and
a processor configured to:
determine information on a desired orientation of the optical imaging system towards at least a part of the object of interest,
obtain the information about the current orientation of the optical imaging system towards at least a part of an object of interest from the one or more information sources,
generate the guidance information based on a mismatch between the desired orientation of the optical imaging system towards at least the part of the object of interest and the current orientation of the optical imaging system towards at least the part of the object of interest, and
control the one or more outputs to provide the guidance information for the user of the optical imaging system, by providing the guidance information via the one or more outputs.
2. The optical imaging system according to claim 1, wherein the object of interest is a body, wherein the one or more information sources are suitable for providing information about a current orientation of the optical imaging system towards at least a part of the body.
3. The optical imaging system according to claim 2, wherein the processor is configured to determine the desired orientation of the optical imaging system towards at least the part of the body based on a pre-operative scan of at least the part of the body.

4. The optical imaging system according to claim 2, wherein the one or more information sources comprise a tissue scanner configured to provide an intra-operative three-dimensional scan of at least the part of the body, wherein the processor is configured to determine the desired orientation of the optical imaging system towards at least the part of the body based on the intra-operative three-dimensional scan of at least the part of the body.

5. The optical imaging system according to claim 2, wherein the one or more information sources are suitable for providing information about a current orientation of the optical imaging system towards a wound, an incision, and/or a surgical site of the body.

6. The optical imaging system according to claim 5, wherein the orientation of the optical imaging system towards the wound, the incision, and/or the surgical site of the body comprises at least one of a distance between the optical imaging system and the wound, the incision and/or the surgical site of the body and a three-dimensional angular orientation of the optical imaging system towards the wound, the incision, and/or the surgical site of the body.

7. The optical imaging system according to claim 1, wherein the one or more information sources comprise a camera configured to provide a camera image of at least the part of the object, the information about the current orientation of the optical imaging system comprising the camera image.

8. The optical imaging system according to claim 7, wherein the processor is configured to process the camera image to determine at least one of a quality of a focus, a utility of a current zoom level, and an alignment of an imaging axis of the camera with at least the part of the object, wherein the processor is configured to control the one or more outputs to provide the guidance information based on at least one of the quality of the focus, the utility of the current zoom level, and the alignment of the imaging axis of the camera with at least the part of the object.

9. The optical imaging system according to claim 7, wherein the processor is configured to detect one or more events or objects within the camera image, wherein the processor is configured to control the one or more outputs to provide the guidance information based on the one or more detected events or objects.

10. The optical imaging system according to claim 1, wherein the one or more information sources are suitable for providing information about one or more current operating settings of the optical imaging system, wherein the processor is configured to determine operating settings of the optical imaging system associated with the desired orientation of the optical imaging system towards at least the part of the object of interest, and to control the one or more outputs to provide the guidance information for the user of the optical imaging system based on a mismatch between the one or more current operating settings of the optical imaging system and the one or more operating settings of the optical imaging system associated with the desired orientation of the optical imaging system.

11. The optical imaging system according to claim 10, wherein the optical imaging system is a surgical microscope, wherein the one or more information sources comprise a control unit of the surgical microscope, wherein the information about one or more current operating settings of the optical imaging system comprises at least one of information about a zoom level of the surgical microscope, information about a working distance of the surgical microscope, and information about an illumination level of the surgical microscope.

12. The optical imaging system according to claim 1, wherein the one or more information sources comprise an accelerometer of the optical imaging system, the accelerometer being configured to provide information about a vibrational movement of the optical imaging system, wherein the processor is configured to control the one or more outputs to provide the guidance information based on the information about the vibrational movement of the optical imaging system.

13. The optical imaging system according to claim 1, wherein the one or more outputs comprise at least one of: one or more displays, one or more indicator lights, one or more vibration modules, and one or more audio outputs.

14. An apparatus for an optical imaging system, the apparatus comprising:
an interface for communicating with one or more information sources of the optical imaging system, the one or more information sources being suitable for providing information about a current orientation of the optical imaging system towards at least a part of an object of interest, and for communicating with one or more outputs of the optical imaging system, the one or more outputs being suitable for providing guidance information for a user of the optical imaging system; and
a processor configured to:
determine information on a desired orientation of the optical imaging system towards at least a part of the object of interest,
obtain the information about the current orientation of the optical imaging system towards at least a part of an object of interest from the one or more information sources,
generate the guidance information based on a mismatch between the desired orientation of the optical imaging system towards at least the part of the object of interest and the current orientation of the optical imaging system towards at least the part of the object of interest, and
control the one or more interfaces to provide the guidance information for the user of the optical imaging system, by providing the guidance information via the one or more outputs.

15. A method for an optical imaging system, the method comprising:
obtaining information about a current orientation of the optical imaging system towards at least a part of an object of interest from one or more information sources of the optical imaging system;
determining information on a desired orientation of the optical imaging system towards at least a part of the object of interest;
generating guidance information based on a mismatch between the desired orientation of the optical imaging system towards at least the part of the object of interest and the current orientation of the optical imaging system towards at least the part of the object of interest; and
controlling one or more outputs of the optical imaging system to provide guidance information for a user of the optical imaging system, by providing the guidance information via the one or more outputs.

16. A non-transitory computer-readable medium storing a computer program comprising instructions which, when the instructions are executed by a processing means for processing the instructions, cause the processing means to perform the method according to claim 15.

* * * * *